United States Patent [19]

Mang

[11] Patent Number: 5,606,968
[45] Date of Patent: Mar. 4, 1997

[54] TRACHEAL OR TRACHEOSTOMY TUBE AND SYSTEMS FOR MECHANICAL VENTILATION EQUIPPED THEREWITH

[76] Inventor: Harald Mang, Haferweg 24a, D-91096 Mohrendorf, Germany

[21] Appl. No.: 362,551

[22] PCT Filed: Jul. 1, 1993

[86] PCT No.: PCT/EP93/01700

§ 371 Date: Mar. 23, 1995

§ 102(e) Date: Mar. 23, 1995

[87] PCT Pub. No.: WO94/01157

PCT Pub. Date: Jan. 20, 1994

[30] Foreign Application Priority Data

Jul. 3, 1992 [DE] Germany ............ 42 21 931.0

[51] Int. Cl.[6] ............................................. A61M 16/00
[52] U.S. Cl. .................. 128/207.14; 128/207.15; 128/204.24; 128/204.25
[58] Field of Search ................... 128/200.26, 207.14, 128/207.15, 207.16, 204.24, 204.25

[56] References Cited

U.S. PATENT DOCUMENTS

| | | | |
|---|---|---|---|
| 1,902,418 | 11/1931 | Pilgrim | 604/43 |
| 4,300,550 | 11/1981 | Gandi et al. | 128/207.18 |
| 4,519,388 | 5/1985 | Schwandom et al. | 128/204.25 |
| 4,584,998 | 4/1986 | McGrail | 128/207.15 |
| 4,646,733 | 3/1987 | Stroh et al. | 128/207.16 |
| 4,690,672 | 9/1987 | Veltrup | 604/43 |
| 4,772,260 | 9/1988 | Heyden | 604/45 |
| 4,850,371 | 7/1989 | Broadhurst et al. | 128/719 |
| 5,108,364 | 4/1992 | Takezawa et al. | 604/43 |
| 5,167,622 | 12/1992 | Muto | 604/35 |
| 5,186,167 | 2/1993 | Kolobow | 128/207.14 |
| 5,255,675 | 10/1993 | Kolobow | 128/207.14 |
| 5,291,882 | 3/1994 | Makhoul et al. | 128/207.15 |
| 5,318,518 | 6/1994 | Plechinger et al. | 604/43 |
| 5,377,671 | 1/1995 | Biondi et al. | 128/204.23 |
| 5,423,313 | 6/1995 | Olsson et al. | 128/207.15 |
| 5,452,715 | 9/1995 | Boussignac | 128/207.15 |

*Primary Examiner*—Aaron J. Lewis
*Attorney, Agent, or Firm*—Antonelli, Terry, Stout & Kraus, LLP

[57] ABSTRACT

The invention relates to a double-barrelled tube with a respiratory (11) and an inhaling (12) passage for the mechanically controllable respiration of a patient in which the inhaling passage connected to a respiratory gas source is fitted at the distal outlet with a nozzle directed towards the distal outlet aperture of the respiratory passage. The respiratory passage is connected at the proximal outlet with an exhalation valve (60) which can be opened and closed by means of an electrical control device. The electrical control device is connected to an electrocardiograph or a blood pressure measuring instrument so that respiration may be effected synchronously with the pulse rate using the respiratory gas fed to the inhalation passage with a retrograde flow of respiratory gas. Inhalation may take place in either the systole or the diastole.

36 Claims, 8 Drawing Sheets

TRACHEAL OR TRACHEOSTOMY TUBE AND SYSTEMS FOR MECHANICAL VENTILATION EQUIPPED THEREWITH

The invention relates to a tube for introduction into the respiratory tract of a patient, especially orotracheal or nasotracheal tubes or tracheostomy tubes for controllable mechanical ventilation of a patient, with a distal end insertable into the respiratory tract and a proximal end provided with connectors and two continuous passages extending essentially from the proximal to the distal end of the tube, one of the two passages serving as a fresh passage in ventilation or breathing and the other of the two passages serving as an inspiration passage for additional or sole administration of fresh gas.

Tracheal and tracheostomy tubes are used for artificial ventilation of a human being in conjunction with ventilators usually comprising an expiration valve and a fresh gas source. The invention therefore consists in an improvement on the tube with a ventilator for improving breathing and for reducing the residual gas remaining in the respiratory tract by using a tube with an improved function.

Artificial ventilation of a human being is normally conducted at the natural respiratory rate. In the various methods of high-frequency ventilation, respiratory rates in the range of the heart rate are also used, without any synchronization of the ventilation phases with the heart action.

The conventional ventilators known heretofore, with a controllable expiration valve and fresh gas supply controllable by means of an electrically controllable pressure-reduction valve, require one tube with a single passage (ventilation tube) or a tube with two passages (inspiration passage, expiration passage) so designed that the gas flow in one passage has no effect on that in the other passage; see DE 25 35 191 A1, AT 389 818. For all practical purposes, known ventilators can be influenced only by damming up the fresh gas source, whereupon any alveolar gas residue remains in the tube in each cycle and has a disadvantageous effect.

The goal of the invention is to eliminate this disadvantage of ventilators with double-lumen tubes. In addition, the control of ventilation is to be effected as a function of signals delivered by an electrocardiograph or a blood pressure monitor for example.

To achieve this goal, according to the invention the tube design proposed in the preamble of claim 1 provides that each of the two passages has a distal outlet opening and the distal outlet opening of the inspiration passage is directed at the distal outlet opening of the ventilation passage. In a preferred embodiment of the tube, the inspiration passage is bent at approximately 180° in the vicinity of the distal end of the tube and directed at or into the distal outlet opening of the ventilation passage and through the ventilation passage to the proximal end of the tube. Preferably, in the tube according to the invention one of the two passages has a cross section smaller than that of the other of the two passages in the tube and the passage with the cross section that is larger than that of the other passage serves as the ventilation passage for ventilation and breathing, and the passage with the cross section that is smaller than that of the other passage serves as the inspiration passage for the additional or sole supply of fresh gas.

The tube according to the invention, which can be designed as an orotracheal, nasotracheal, or tracheostomy tube, has two passages so designed that conventional ventilation can be conducted through the ventilation passage (for example, intermittent positive pressure ventilation, or IPPV). In addition, endotracheal and endobronchial suctioning can be performed through this passage both with conventional disposable suction catheters and with a bronchoscope. The inspiration passage, made with a smaller cross section than that of the ventilation passage, is intended for additional or sole supply of fresh gas to the patient. Both the additional and sole gas supply through the inspiration passage can be provided intermittently, preferably on expiration, or constantly or continuously, but as a function of the fresh phase with a different current, also termed flux or flow. The distal end of the tube, which is placed in the trachea, is designed so that the inspiration passage narrows to form a jet and its opening or openings point or extend toward or into the open distal outlet end of the ventilation passage. In other words, the nozzle-shaped distal end of the inspiration passage "blows" into the outlet opening of the ventilation passage, namely in the expiration direction through the ventilation passage at the proximal end of the tube, in other words out of the trachea and hence out of the patient. At the proximal end of the tube, outside the trachea, both passages in the tube have connections (connectors) for the connecting lines to the fresh gas sources, valves, or other equipment being used.

As a result of the design according to the invention for the distal end of the inspiration passage, which serves to supply the fresh gas, in the shape of a nozzle, the gas flowing through the inspiration passage is deflected through 180° so that it is guided from the distal end of the tube into the ventilation passage of the tube in the direction of its proximal end and flows toward the proximal end. To achieve a jet effect using the jet pump principle, the cross sectional area of the inspiration passage of the tube is reduced at the distal end up to the nozzle outlet opening, preferably by approximately one-half.

When the tube according to the invention is used for the ventilation of a patient, as a result of a continuous supply of fresh gas through the smaller passage, the dead space during ventilation can be considerably reduced, i.e. the volume of residual gas that is not expired is reduced considerably. In order to improve ventilation during mechanical ventilation of a patient, it is even possible with the tube according to the invention to reduce the dead space, thus increasing carbon dioxide elimination by administering a continuous retrograde or expiratory retrograde fresh gas flow through the smaller tube passage.

In the tubes according to the invention, with two passages of different sizes, the larger passage is intended to permit both unimpeded conventional ventilation and spontaneous breathing by the patient. In addition, the larger passage is intended to allow cleaning up the bronchi with suction catheters or with a bronchoscope. The smaller passage of the tube is used to supply the fresh gas. Its cross sectional area is therefore selected so that with each size of tube correct for the patient, up to five times the spontaneous fresh minute volume can be supplied with assumed pressures as behind commercially available flow regulators associated with fresh gas sources.

For example, the following cross-sectional ratios can be given as guidelines: larger passage (fresh passage) to smaller passage (inspiration passage) to nozzle outlet opening, 8:2:1. In tubes for adults, the cross sectional area of the larger passage should correspond to that of a conventional tube with an inside diameter of 7 mm, i.e. approximately 38.5 $mm^2$. The smaller passage of the tube at 9.6 $mm^2$ then corresponds to an inside diameter of a conventional tube with an inside diameter of 3.5 mm. The cross-sectional area of the nozzle outlet opening of the smaller passage in this example is then 4.8 $mm^2$.

Advantageous embodiments of the tube according to the invention are shown in the characterizing features of sub-claims 2 to 21.

The tubes can be made with or without a cuff. The cuff can be inflatable (balloon) or unfold by itself (so-called "foam cuff"). When no cuff is provided, so-called "gills" can be used which are wafer-thin membranes or structures made of silicone, arranged in a circle around the shaft of the tube for sealing.

The tubes themselves are made of a tissue-compatible plastic, for example PVC, preferably a plastic that does not change in the body even when left there for a long period of time and can be disposed of in an environmentally safe manner after use. It is also possible to use spiral-reinforced tubing made of rubber or silicone (according to Woodbridge). For optimum utilization of the cross-sectional area of the tube, its wall should be as thin as possible.

To achieve a jet effect with the aid of the nozzle formed at the distal end of the inspiration passage as well as the deflection of the flow in the inspiration passage in the direction of the ventilation passage, entering the distal end thereof, the nozzle outlet opening of the inspiration passage can project slightly into the outlet opening, i.e. into the ventilation passage, or be arranged in front of the outlet opening of the ventilation passage or directly adjoining it. The arrangement of the outlet opening of the ventilation passage and the nozzle outlet opening of the inspiration passage should leave sufficient space for entrainment of the expired gas, but at the same time must not block the outlet opening of the ventilation passage so that unimpeded flow is possible during ventilation and a suction catheter can also be passed through the ventilation passage of the tube, for example.

To achieve a Venturi effect which increases the volume of gas dram out of the respiratory tract, a bead (short reduction of the cross-sectional area up to about 25%) can be located in the (distal) inlet area of the ventilation passage near the patient.

The nozzle-shaped element that forms the nozzle at the distal end of the tube of the inspiration passage that is near the patient likewise consists of a tissue-compatible plastic that can be disposed of in an environmentally safe manner, with a harder material being used than for the tube itself. The nozzle or the nozzle-shaped body has a defined seat relative to the tube, for example by means of a snap closure; it is also glued or welded to the tube.

The double-lumen tube according to the invention with a nozzle at the distal outlet of the inspiration passage, which blows into the ventilation passage from the distal end thereof, can be used to support ventilation with a continuous retrograde fresh gas flow or an exhalational retrograde fresh gas flow or for ventilation with a continuous retrograde fresh gas flow. Fresh gas can be air or oxygen supplied from a gas source, additionally equipped with a flowmeter for compressed air or oxygen. Mechanical ventilation in addition to the double-lumen tube inserted into the trachea of a patient and the fresh gas source also requires a controllable expiration valve connected to the proximal end, in other words the end of the larger passage of the tube away from the patient. The expiration valve, the fresh gas source, a pressure reduction valve in the fresh gas supply, and a tube constitute a ventilator.

Controlled or assisted ventilation is performed in the usual manner through the ventilation passage, in other words the larger passage on the tube. To improve ventilation, i.e. to increase carbon dioxide elimination by reducing dead space, a continuous, preferably exhalational fresh gas flow can be added through the inspiration passage of the tube. Basically, air or oxygen can be fed continuously into the smaller passage of the tube using the ventilator. Then, besides the double-lumen tube, only one flowmeter is needed for compressed air or oxygen as fresh gas from the fresh gas source.

For ventilation with a continuous retrograde gas flow, according to the invention an electrical control device is provided for the controllable expiration valve associated with the proximal outlet of the ventilation passage of the tube. The control device utilizes electrical signals delivered from the ventilator and opens the expiration valve for continuous retrograde gas flow during the exhalation phase, i.e. whenever the expiration valve is in the "open" position.

Naturally the inspiratory oxygen concentration of the continuous or exhalational retrograde gas flow can also be identical with the respiratory oxygen concentration supplied through the ventilator or the fresh unit, i.e. through the fresh gas source. This is accomplished by connecting the flowmeter for the continuous or exhalational retrograde gas flow to the air/oxygen mixer of the fresh gas source or to a separate air/oxygen mixer with the same setting. The fresh gas for the continuous or exhalational retrograde gas flow can be heated and moistened in the same way as is done for a gas delivered by a ventilator. In particular, ventilation of a patient with a ventilator using the double-lumen tube according to the invention is possible with a continuous retrograde fresh gas flow. If, to support ventilation with a continuous retrograde gas flow, one begins at the level of a fraction of the required minute volume and the continuous retrograde gas flow is increased with a simultaneous reduction of conventional ventilation up to a multiple of the minute volume originally required for conventional ventilation, a point is eventually reached at which conventional ventilation using the fresh passage of the tube can be completely suspended. All of the fresh gas then flows through the inspiration passage of the tube into the trachea and is distributed, with the expiration valve closed, into the lungs—inspiration—or escapes with the expiration valve open together with the gas that flowed into the lung during the inhalation phase, outward through the ventilation passage of the tube—expiration. This type of ventilation is termed ventilation with a continuous retrograde gas flow.

In its simplest from, ventilation with a continuous retrograde gas flow can be performed manually. Then the fresh gas source is connected to the smaller passage of the tube (fresh gas flow 10 l/min for example) and the person administering ventilation manually closes the outer opening of the fresh passage of the tube (inhalation phase) for 3 seconds for example and then releases it again (exhalation phase), for example for 3 seconds as well, so that a minute volume of 5 liters is obtained in this example.

In theory, any conventional ventilator with a time-controlled expiration valve and fresh gas source can be used for ventilation with a continuous retrograde gas flow. The gas connections of the ventilator are then not used and the device is merely supplied with current. The inspiration passage of the tube is connected with the fresh gas source and the ventilation passage of the tube is connected through a connecting hose with the expiration valve. On the ventilator the inhalation/exhalation ratio and the respiratory rate or the inhalation and exhalation times can be adjusted directly. The level of the required continuous retrograde gas flow for efficient carbon dioxide elimination then depends on the respiratory rate and the inhalation/exhalation ratio. The mean airway pressure critical for oxygenation is adjusted by changing the inhalation/exhalation ratio and the PEEP valve or the PEEP function of the ventilator. Therefore a suitable time-controlled expiration valve is required. The task of a time-controlled expiration valve with positive end exhalation pressure function can also be supplied by an expiration valve that is independent of a ventilator, said valve being usable in cases when ventilation with a continuous retrograde fresh gas flow is conducted exclusively in a patient.

The double-lumen tube according to the invention and the principle of ventilation with a continuous retrograde gas flow with a ventilator reduce the dead space when ventilating a patient in such a way that ventilation can be conducted at respiratory rates that are much higher than those conventionally employed. It is then possible according to the invention, by conducting ventilation with a continuous retrograde gas flow and using the tube designed according to the invention, to work at respiratory rates that correspond to the human heart rate. According to the invention therefore the double-lumen tube is used in a ventilator that makes it possible to perform ventilation with a continuous retrograde gas flow that is EKG—triggered and in synchronization with the pulse.

For this purpose, according to the invention a ventilator is proposed using the double-lumen tube according to the invention according to claim 24. According to the invention the electrical control device receives the output signals from conventional electrocardiographs or blood pressure monitors to close and open the expiration valve which is available in conventional ventilators or as a device by itself in synchronization with the pulse.

With a ventilator system equipped according to the invention, the inspiration phase can be synchronized with the systole. This measure is capable of lowering the afterload of the left ventricle, which is hemodynamically favorable in left ventricular heart failure (e.g. myocardial infarction). It is also possible to synchronize the inhalation phase with the diastole, and as a result the right ventricle does not have to eject the blood against a high vascular resistance into the pulmonary circulation compressed by the respiratory pressure. This measure reduces the load on the right ventricle which has an advantageous effect in all conditions involving acutely elevated pulmonary vascular resistance, e.g. pulmonary embolism.

Advantageous improvements on the ventilator using the double-lumen tube according to the invention and an electrical control device for the expiration valve can be obtained from the characterizing features of claims 25 to 36.

Integration of an electrocardiograph into the ventilator makes it possible, using the signals from the electrocardiograph, to control the expiration valve connected to the larger passage of the tube in such a way that ventilation takes place in synchronization with the pulse, using a fresh gas supplied through the inspiration passage of the tube, a so-called pulse-synchronized positive pressure ventilation. The control device for the expiration valve is also equipped with functions for changing the time relationship from inspiration to expiration (inhalation/exhalation ratio) and for the alternative selection of synchronization of inhalation with a contraction of the heart muscle (systolic inhalation) or with its relaxation (diastolic inhalation).

In another embodiment of the invention, an electrically controllable valve, especially a pressure-reduction valve, is provided, arranged in the supply line from the fresh gas source to the inspiration passage of the tube, and the fresh gas flowing to the inspiration passage of the tube can be metered with its aid so that the gas flow during inhalation and gas flow during exhalation may be freely selected.

During mechanical ventilation with a continuous retrograde gas flow, a constant fresh gas flow can be set for the sake of simplicity. Advantageously, however, there is the possibility of adjusting the magnitudes of the continuous fresh gas flow for the inhalation phase and for the exhalation phase separately. The electrically controllable pressure-reduction valve is provided for this purpose. The inhalational gas flow can be adjusted to the minute volume required for carbon dioxide elimination and the exhalational gas flow can be adjusted to the mean airway pressure critical for oxygenation.

The design of the tube according to the invention as well as a system according to the invention for pulse-synchronized ventilation with retrograde gas flow will now be described and explained with embodiments.

Figure 1:
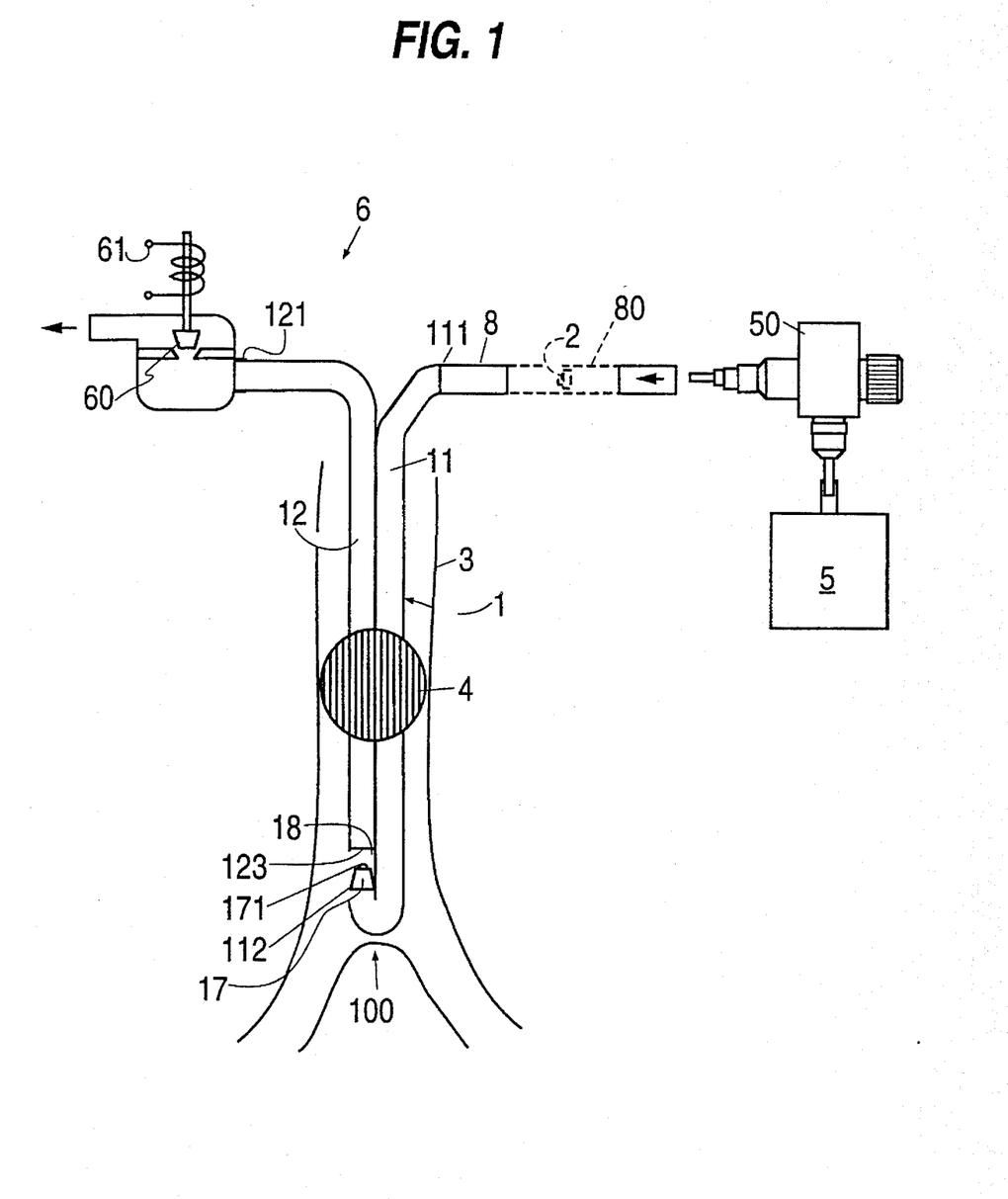
FIG. 1 is a schematic diagram of a ventilator system.
Figures 2, 6:
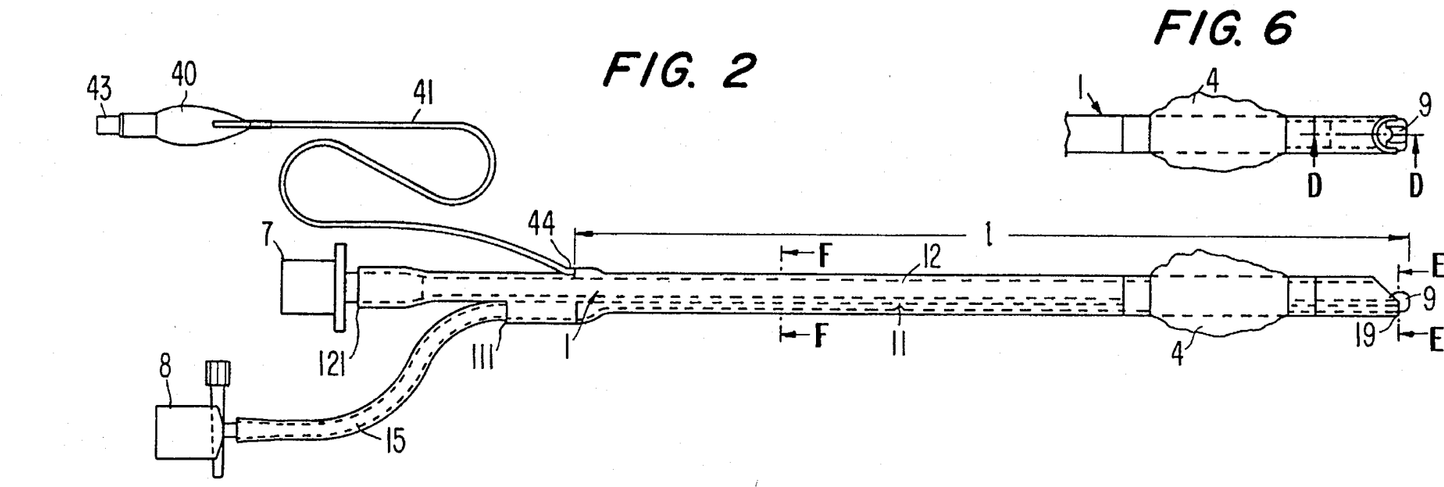
FIG. 2 is a view of a double-lumen tube with nozzle.
FIG. 6 is a top view of the end area of the tube according to FIG. 2.
Figure 3:
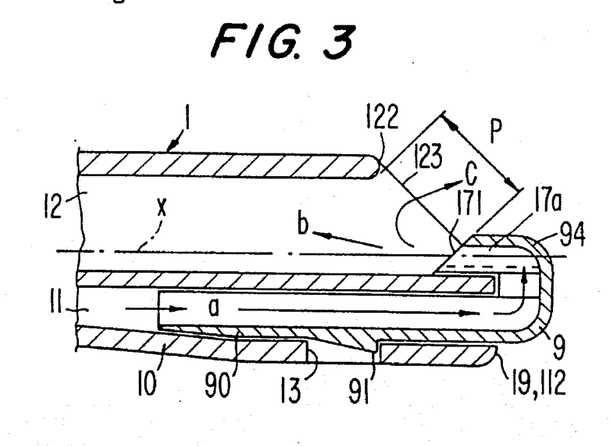
FIG. 3 is a partial cross section DD in FIG. 6 of the distal end area of the tube.
Figure 4:
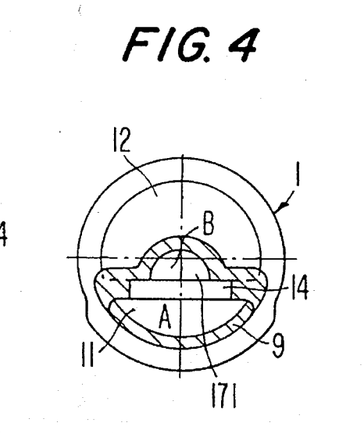
FIG. 4 is view EE in FIG. 2.
Figure 5:
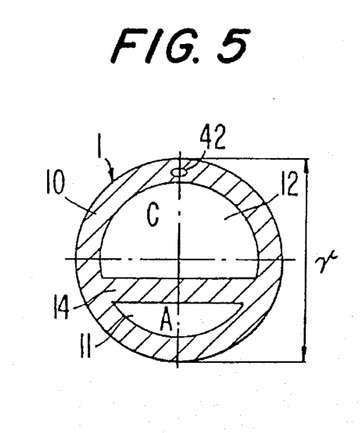
FIG. 5 shows cross section FF in FIG. 2.
Figures 7, 9:
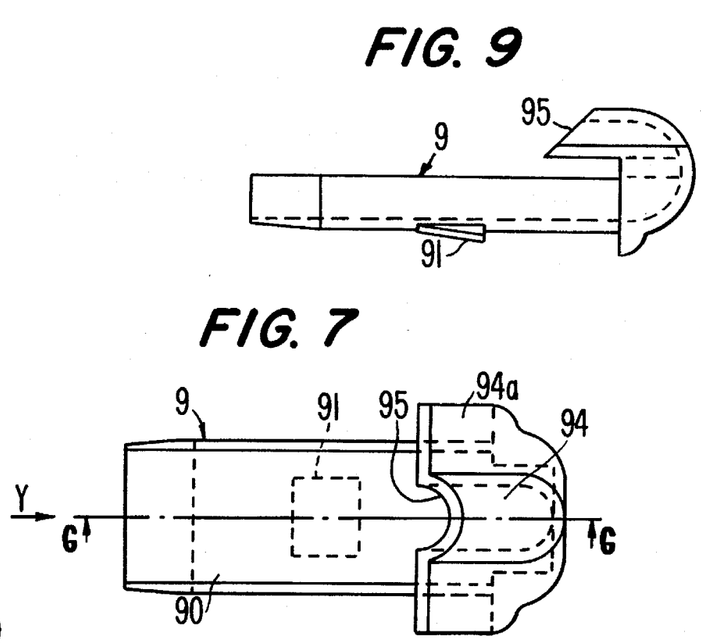
FIG. 7 is a nozzle-shaped body for insertion into the inspiration passage of the tube according to FIG. 2, in a top view.
FIG. 9 is a side view of the nozzle-shaped body according to FIG. 7.
Figure 8:
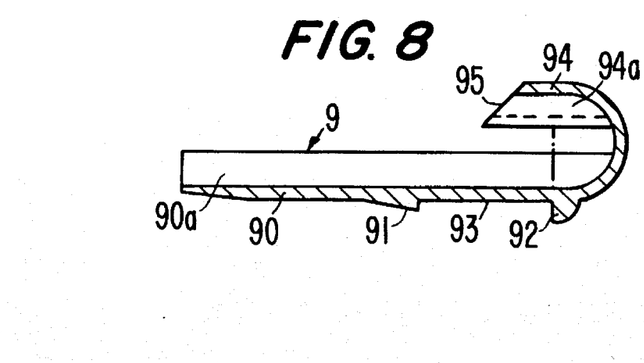
FIG. 8 is a cross section GG through the nozzle-shaped body according to FIG. 7.
Figure 10:
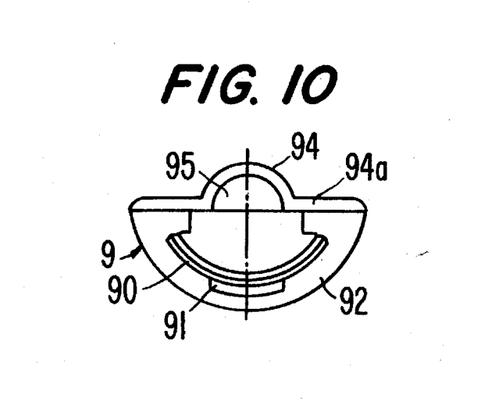
FIG. 10 is a view Y of the nozzle-shaped body according to FIG. 7.

FIG. 1 shows schematically a ventilator 6 with double-lumen tube 1, fresh gas source 5 with flowmeter 50, and a controllable pressure reduction valve 2 in gas supply line 80 to tube 1 and an electrically controllable expiration valve 60 with electrical connections 61. Tube 1 inserted into the trachea 3 of a patient up to carina 100 has two continuous passages 11 and 12, of which passage 11 used as the inspiration passage has a smaller cross section than passage 12 used as the ventilation passage. The ventilator system 6 shown is suitable for controlled mechanical ventilation of a patient. The double-lumen tube according to FIG. 1 has an inflatable cuff 4 for holding and sealing in trachea 3. Inspiration passage 11 is connected on the inlet side, in other words proximal end 11, through a connector 8 and through flowmeter 50 to a fresh gas source 5. The fresh gas is under a desired positive pressure. Ventilators with tubes not according to the invention are known.

Ventilation passage 12 is connected on the output side, i.e. at proximal end 121, with electrically controllable expiration valve 60.

In the vicinity of distal end of tube 1, near carina 100, inspiration passage 11 and exhalation passage 12 are connected together by a nozzle 17 formed at the distal end 112 of the inspiration passage. Conical nozzle 17 has its nozzle outlet opening 171 or nozzle mouth close to or at outlet opening 123 of ventilation passage 12, so that an open annular space 18 remains between the nozzle outlet and the distal end of ventilation passage 12 and/or the inside wall of ventilation passage 127. With expiration valve 60 closed, the fresh gas, which is under pressure, fills the lung through inspiration passage 11 of tube 1, emerging at nozzle 17. With expiration valve 60 open, the fresh gas flows through nozzle 17 into ventilation passage 12 from the distal end and outward through ventilation passage 12 and expiration valve 60. During this process, the gas in the lung is simultaneously expelled by the vacuum prevailing in free annular space 18 through ventilation passage 12 and expiration valve 60. Nozzle 17 at the distal end of inspiration passage 11 is arranged so that it is directed at the distal end of the ventilation passage and blows into the ventilation passage from the nozzle of the inspiration passage, in the exhalation direction.

Between gas source 5 and inspiration passage 11 of tube 1, an electrically controllable pressure reduction valve 2, shown by the dashed lines, can be inserted which makes it possible to provide different fresh gas pressures for the inhalation phase and the exhalation phase. In this way, the exhalation process can be accelerated timewise for example.

The additional design of ventilator system 6 according to the invention according to FIG. 1 for controlled mechanical ventilation consists in controlling expiration valve 60 as a function of a signal from an electrocardiograph. The system thus equipped then makes it possible to perform ventilation with positive pressure in synchronization with the heart cycle. For example, the efficiency of the failing left ventricle can be improved by systolic inhalation, so-called afterload reduction and diastolic exhalation, so-called minimization of preload reduction. Likewise, in situations with acute fight ventricular failure the fight ventricle can be relieved by diastolic inhalation and systolic exhalation.

Depending on the therapeutic goal, electrically controllable expiration valve 60 and/or electrically controllable pressure-reduction valve 2 can be controlled by signals controlled in turn by medical instruments, as for example an electrocardiograph, or by a clock that replaces these devices.

In FIGS. 2 to 6, a double-lumen tube 1, suitable for use in controlled mechanical ventilation with a continuous retrograde gas flow, is shown. Tube 1 has two through passages 11, 12 separated from one another by a partition 14; see FIG. 3. The through passages have different sizes, with the larger passage serving as a ventilation passage for unimpeded conventional ventilation as well as spontaneous breathing by the patient, and in addition must be sufficiently large in cross section to permit introduction of a suction catheter or bronchoscope. Smaller passage 11 serves as the inspiration passage for supplying the fresh gas. Tube 1 is long enough so that regardless of the size of the tube or patient, a portion of the shaft of the tube projects from the patient and is suitable for fastening, preferably with adhesive or hook-and-loop fasteners. The length 1 of an average tube is 220 mm for example. In the vicinity of the distal end 19 of the tube, at a slight distance from the latter, an inflatable tube cuff is provided. Tube cuff 4 is supplied with inflating air through an air supply duct 42 formed in the wall of tube 10; see FIG. 5. In the vicinity of the proximal end of tube 1, control balloon 40 is mounted with a connection 43 through air supply hose 41 to the output 44 of air channel 42. At the proximal end 121 of larger passage 12, a suitable connecting stub 7 is provided. At the proximal outlet 11 of inspiration passage 11 a connecting stub 8 is likewise provided that, for the sake of improved handling, is connected through a supply tube 15 with the proximal input of the inspiration passage. At the distal end 19 of tube 1, inspiration passage 11 is designed to be tapered in the form of a nozzle, see FIGS. 3 and 4, with the nozzle channel of nozzle 17 being bent at 180° so that nozzle outlet opening 171 points at the open distal end 122 of ventilation passage 12. The fresh gas flow flowing through inspiration passage 11, see FIG. 3, in the direction of arrow a is guided at the distal end of tube 19 by the design of noble 17 with a cross section that decreases relative to the cross section of inspiration passage 11 toward the outlet of the nozzle, with a simultaneous deflection by 180° in the direction of ventilation passage 12, with simultaneous acceleration, and flows in the direction of arrow b, i.e. in the opposite direction, from the distal end of the tube into fresh passage 12. For those cases in which the expiration valve (see FIG. 1) is closed at the proximal outlet of passage 12, the gas flowing in the direction of arrow b into the ventilation passage, after filling ventilation passage 12, can escape through distal outlet opening 123 of ventilation passage in the direction of arrow c and reach the lung. When the expiration valve is open at the proximal outlet of ventilation passage 12, on the other hand, the gas flow moving in the direction of arrow b into ventilation passage 12 from the distal end thereof entrains the exhalation gas coming from the lungs and clears the lungs well to remove exhalation gas and improve ventilation considerably, i.e. increase carbon dioxide elimination by reducing dead space.

In the example shown in FIGS. 2 to 6, the design of distal end 112 of inspiration passage 11 with a nozzle is shown, with deflection of the flow channel with the aid of a nozzle-shaped piece 9 inserted into the distal end of the tube and inspiration passage 11. Nozzle-shaped piece 9 has a leg 90 abutting the wall of tube 10 internally, so that a flow channel continuing inspiration passage 11 is formed between partition 14 and leg 90. Nozzle-shaped piece 9, as an extension of leg 90, is made hook-shaped with a shorter leg 94 guided around the distal end of the partition, leaving a space forming nozzle channel 17a. Nozzle channel 17a terminates with a flow direction that runs axially parallel to lengthwise axis X of the tube. The outlet opening 171 of the nozzle channel and hence of the inspiration passage 11 at the distal end is shown doubled outward in the example shown in FIG. 3, making improved outward flow in arrow direction c during inhalation possible. In addition, nozzle outlet opening 171 of inspiration passage 11 is located at the periphery of the cross section of ventilation passage 12 so that an outlet opening 123 that is as large as possible remains for ventilation passage 12. This outlet opening 123, for example in the example shown, can have a diameter p of 5.9 mm. Tube wall 10 should be as thin as possible; when a suitable material is selected, for example PVC, it can be 1.2 mm. Outlet opening 123 must also be large enough to permit unimpeded introduction of a suction catheter through ventilation passage 12 to evacuate the respiratory tract. For this reason, outlet opening 123, also beveled, for example at 45° relative to the lengthwise axis X of tube 1, in such fashion that the tip of the tube is tapered at one end toward distal end 19. In this manner as well outlet opening 123 is made larger. It is also possible, by further separation of distal outlet opening 123 of ventilation passage 12 and distal outlet opening 171 of inspiration passage 11, to increase the outlet area, with reference being made for example to the embodiment shown in FIG. 11, where outlet openings 123 and 171 contact one another only in foot area FP at partition 14.

Nozzle-shaped piece 9 is mechanically engaged in the vicinity of tube wall 10 by means of a projecting locking nose 91 that engages a recess 13 in the tube wall. In addition, tubular-shaped piece 9 is glued or sealed in the area of tube wall 10.

For the double-lumen tube to function well, especially with good ventilation and gas direction, the sizes of the cross sections of the ventilation passage, the inspiration passage, and the nozzle outlet opening, individually and in relation to one another, are critical. The cross section of the inspiration passage must be sufficiently large to permit a fresh gas supply sufficient for up to five times the spontaneous minute ventilation to pass through at usual pressure. The cross section of the ventilation passage must permit unimpeded conventional ventilation or spontaneous breathing by the patient, and the passage of a suction catheter. Under these circumstances, a ratio of cross section C of the ventilation passage to the cross section A of the inspiration passage to the size B of nozzle outlet opening 171 of the inspiration passage of approximately 8:2:1 is provided. Cross sections A, B, C, as stated above, are evident from the cross sections shown in FIGS. 4 and 5 for the catheter according to FIG. 2. With an inside diameter of ventilation passage 12 corresponding to a conventional tube with an inside diameter of 7 mm, the cross-sectional area C is approximately 38.5 mm$^2$, cross-sectional area A is approximately 9.6 mm$^2$, and nozzle outlet area B is approximately 4.8 mm$^2$. Accordingly, the outside diameter r of tube 1 is approximately 11 mm.

As connectors for inspiration passage 11, preferably those with integrated tapping stubs for monitoring airway pressure or gas composition can be used, possibly also for the proximal entrance of ventilation passage 12.

Figure 11:
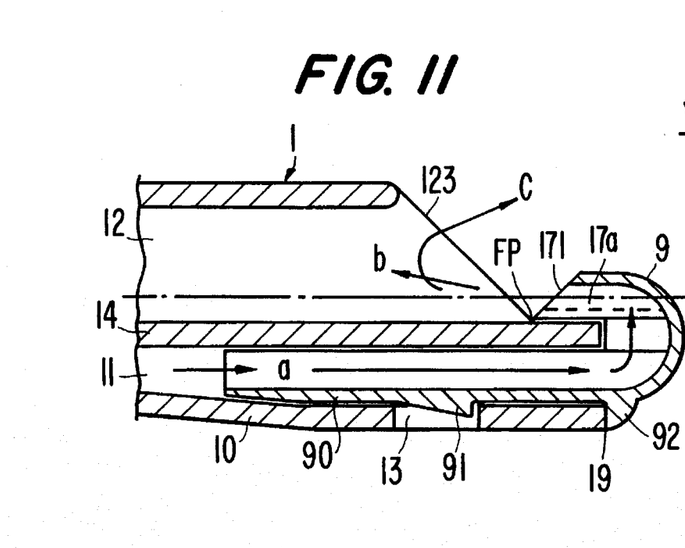
FIG. 11 is a partial lengthwise section of the distal end area of the tube, with the nozzle-shaped body according to FIGS. 7 to 10 inserted.

In FIGS. 7 to 10, another version of a nozzle-shaped piece 9 for insertion into inspiration passage 11 for forming a nozzle outlet opening at the distal end of tube 1 is shown. The nozzle-shaped piece likewise has a long leg 90 for insertion into inspiration passage 11 from the distal end 19 of the tube, as shown in FIG. 11, while tube wall 10 is expanded outward corresponding to the thickness of leg 90 in order to continue inspiration passage 11 with the same cross section at the beginning of the nozzle-shaped piece. The nozzle-shaped piece also has leg 94 bent at 90°, which leads to a bend in the flow channel by 180° and ends with a bevel 95 at the outlet opening. The channel enclosed by short leg 94 has a cross section that tapers and narrows toward end 95, thanks to additional bends 94a. In connection with partition 14, the closed flow channel for the fresh gas in the direction of arrow a is then formed; see FIG. 11. To anchor nozzle-shaped piece 9 to tube 1, externally on the longer leg, projecting locking hook 91 and stop lug 92 with receiving pocket 93 for locking, see FIG. 11, are formed on tube wall 10. Depending on the arrangement of nozzle outlet opening 17 1 formed by nozzle-shaped piece 9, mounted at the tube end, according to FIG. 11, for inspiration passage 11, and the design of nozzle outlet opening 123 of ventilation passage 12, corresponding ventilation is made possible as indicated by arrows c and b for the fresh gas supplied through inspiration passage 11.

Figure 12:
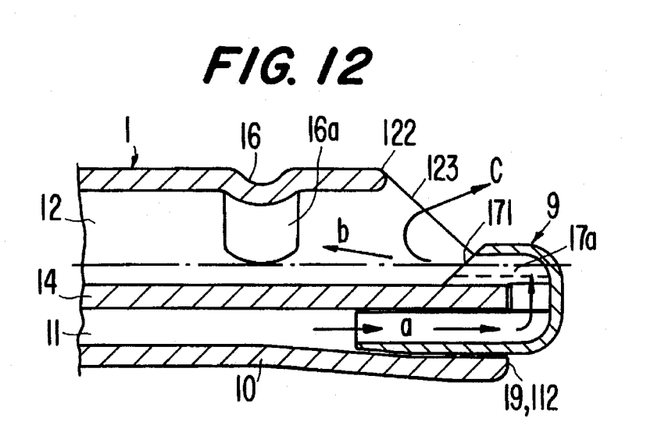
FIG. 12 is a partial lengthwise section through the distal end area of the tube, with insertion of a varied nozzle-shared body and bead formation.

FIG. 12 shows another variation on a nozzle-shaped piece 9 for forming the nozzle-shaped constriction at the distal end of the inspiration passage and nozzle outlet opening 171, inserted at the distal end 19 of tube 1. In this case, only a relatively short nozzle-shaped section has its long leg 9 inserted into the expanded end of the tube into inspiration passage 11 and glued therewith.

To achieve a Vemuri effect, intended to increase the volume of gas entrained by gas flow b from the respiratory tract, near distal outlet opening 123 of ventilation passage 12 a bead 16a can be impressed into the ventilation passage for reducing the cross section by means of a notch 16 in wall 10 of the tube. A reduction of the cross section by up to about 25% can be achieved in this manner.

Figure 13:
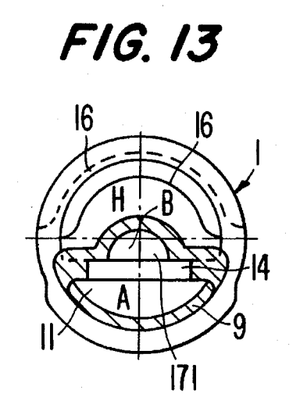
FIG. 13 is a section similar to section EE in FIG. 2 of the end of the tube according to FIG. 12.
Figure 14:
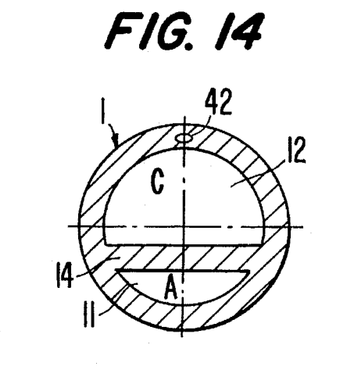
FIG. 14 is a cross section through the tube according to FIG. 12 corresponding to FIG. 5.

FIG. 13 is a view of the distal end 19 of the tube in cross section, where H represents the cross-sectional area of ventilation passage 12 reduced by bead 16a.

Figures 15, 16:
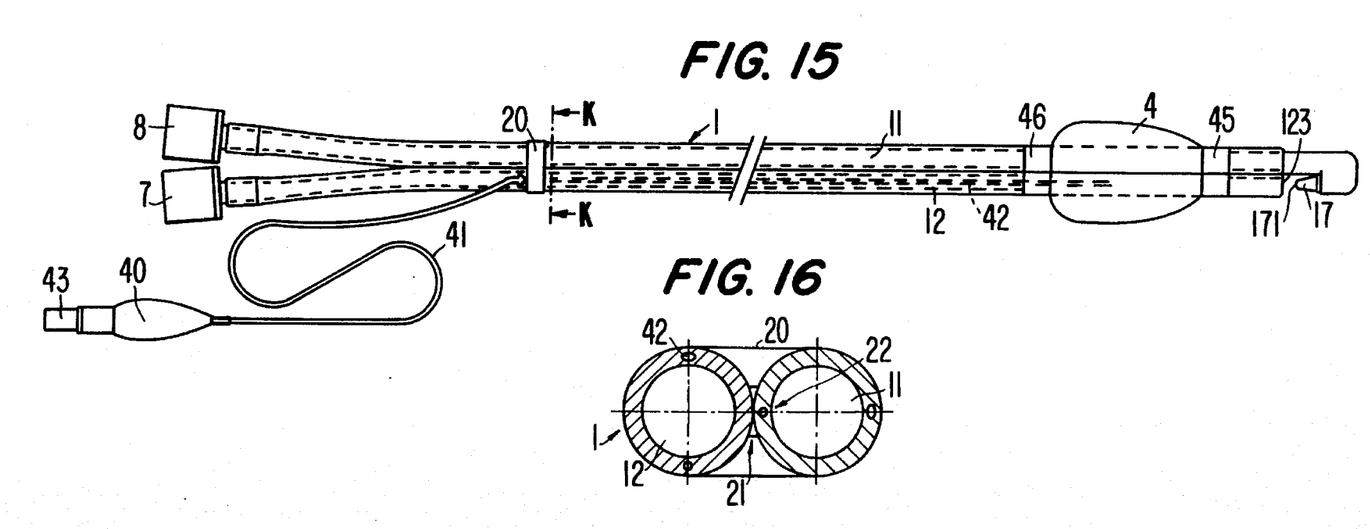
FIG. 15 is a view of a double-lumen tube in a double-tube design.
FIG. 16 is a cross section KK through the tube according to FIG. 15.

FIG. 15 shows a design of double-lumen tube with two pipes brought together to form one tube, containing the smaller inspiration passage 11 and the larger ventilation passage 12. The two pipes containing the passages are connected together by strips 20 and strips 45, 46 in the vicinity of inflatable tube cuff 4. In addition, the pipes forming tube 1, see the cross section in FIG. 16, can be permanently connected to one another by gluing in contact area 22. It is also possible to weld them together in this area by using a suitable plastic, for example by using solvents. In tube 1 according to FIG. 15, outlet opening 171 of the end of the nozzle-shaped inspiration passage that is bent to an angle of 180° is located a short distance from the distal outlet opening 123 of ventilation passage 12, so that a free outward flow of the gas emerging from the nozzle outlet opening 171 into the lungs can take place with the expiration valve closed, and distal outlet opening 123 is sufficient to pass a suction catheter through and also, with the expiration valve open, the gas flow from nozzle outlet opening 171 can blow directly into outlet opening 123 into large ventilation passage 12.

Figure 17:
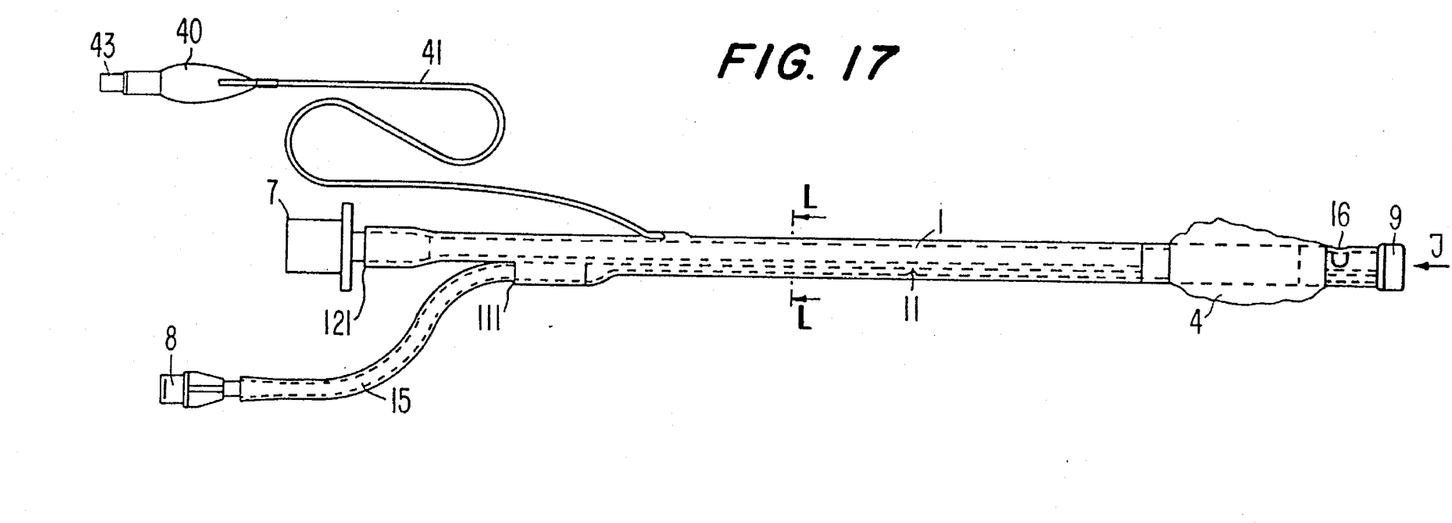
FIG. 17 is a view of a double-lumen tube with an annular nozzle mounted at the distal end of the tube.

FIG. 17 shows another embodiment of double-lumen tube 1 according to the invention, in which the distal end of tube 1 is provided with an annular nozzle-shaped section that forms both the tapering nozzle outlet channel at the distal end for inspiration passage 11 and also outlet opening 123 of ventilation passage 12 at the distal end.

Figure 18:
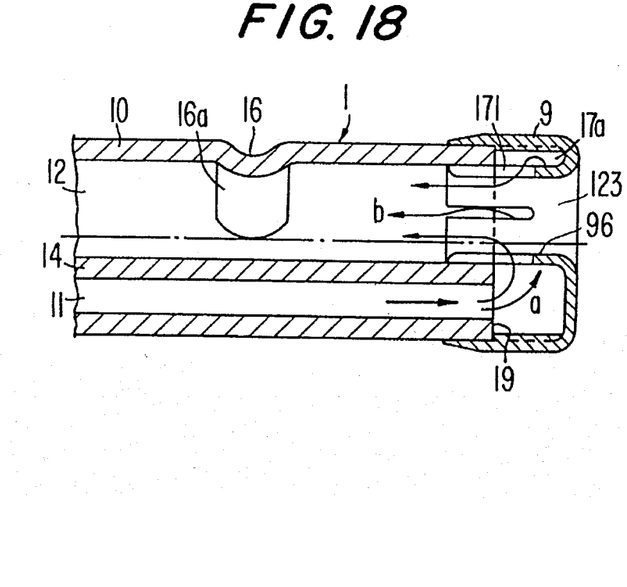
FIG. 18 is a partial lengthwise section through the distal end area of the tube according to FIG. 7 along section MM in FIG. 19.
Figure 19:
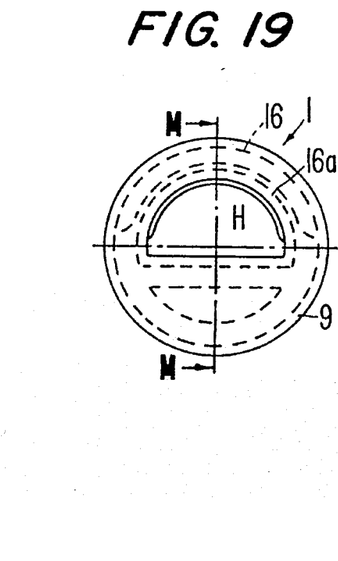
FIG. 19 is a view I of the distal end of the tube according to FIG. 17.

FIG. 19 shows view I according to FIG. 17 looking at the distal end of the tube with nozzle-shaped piece 9. In FIG. 18, axial lengthwise section MM shows in FIG. 18 the distal end area of the tube in cross section and the annular molded part 9, which is attached externally to tube wall 10 and fits over it, and internally forms a tapering annular space with a plurality of nozzle outlet openings 171. Inner nozzle annular wall 96 also forms the limit for outlet opening 123 of the ventilation passage. At a slight distance from distal end 19 of tube 1, once again in the vicinity of ventilation passage 12, a notch 16 is provided to form a bead 16a that reduces the cross section partially and over a short distance.

Figure 20:
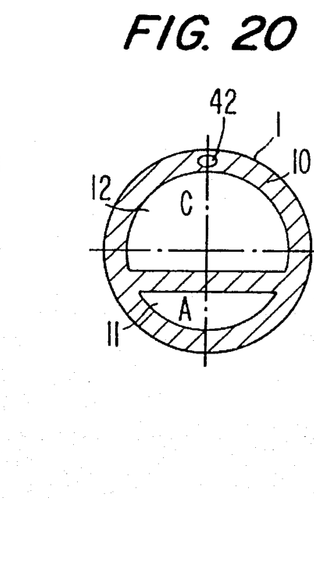
FIG. 20 is a cross section LL of the tube according to FIG. 17.

FIG. 20 shows that the tube in the middle area, see cross section LL in FIG. 17, has continuous fresh passage 12 with cross section C and continuous inspiration passage 11 with cross section A, of a size sufficient to perform its functions.

For pulse-synchronized ventilation with a continuous retrograde gas flow, expiration valve 60 of ventilator 6 according to FIG. 1 is controlled by means of a control device. For pulse-synchronized ventilation, the control device is connected to an electrocardiograph EKG whose EKG signal is received by the control device, processed electronically, and used as the control signal for the expiration valve.

Figure 21:
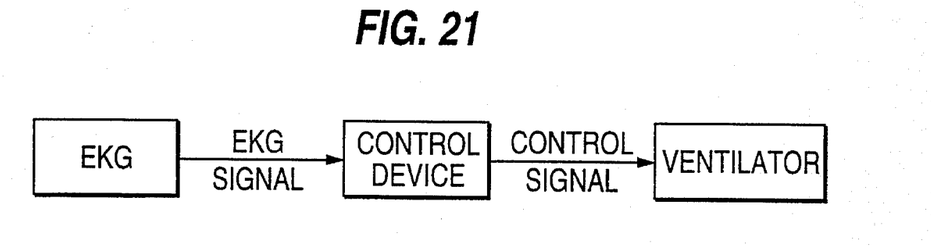
FIG. 21 is a block diagram of a control device for the ventilator system according to FIG. 1.
Figure 22:
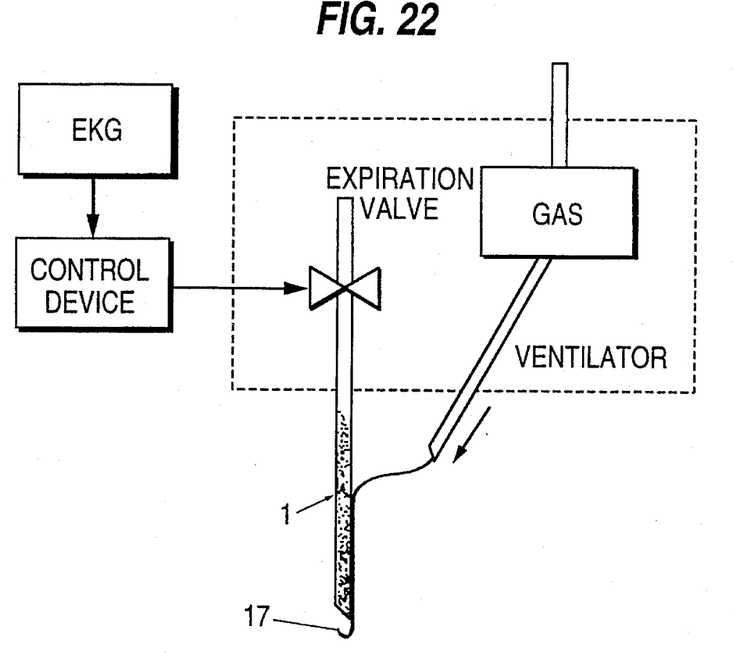
FIG. 22 is a functional diagram of the control device with ventilator.

FIG. 21 is a block diagram of the functional layout. The control device forms a connection between the EKG or the blood pressure measuring device and the expiration valve of a ventilator and delivers the control signal to open or close the expiration valve. The basic system of a ventilator system for pulse-synchronized ventilation is shown schematically in FIG. 22 and includes the following parts: a gas source, a double-lumen tube with a nozzle at the distal end of the inspiration passage, an expiration valve, a control device, and an electrocardiograph or blood pressure measuring device. The ventilator system can be equipped with conventional EKG units or blood pressure measuring devices as well as commercially available ventilators with an expiration valve, for example a Siemens Servo Ventilator 900C in conjunction with the electronic adaptable control device according to the invention and in conjunction with the double-lumen tube according to the invention, with a nozzle outlet at the distal end of the inspiration passage and permits pulse-synchronized ventilation for anesthesia, intensive care, and emergency medicine.

Figure 23:
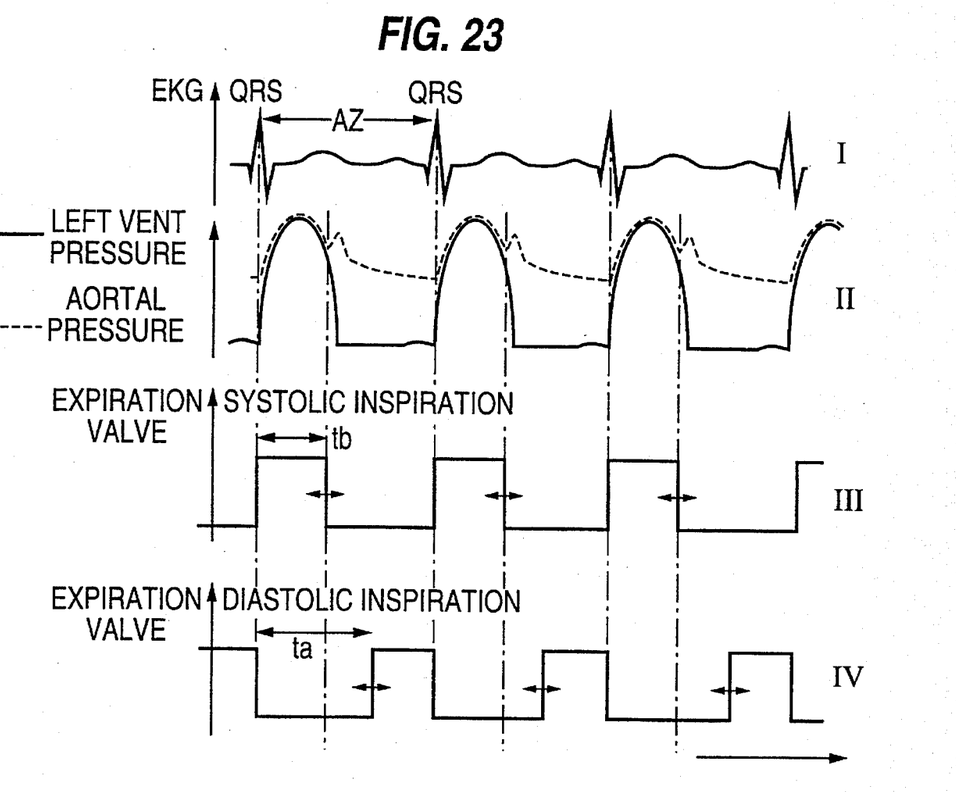
FIG. 23 is a diagram showing the control of the expiration valve by means of signals from an electrocardiograph.

The charts for pulse-synchronized ventilation are shown in FIG. 23. Curve I shows the EKG signals with the QRS complexes obtained by the EKG. The time duration AZ calculated from time interval AZ between two QRS complexes corresponds to the duration of one fresh cycle. Curve II shows the changes in pressure in the aorta and in the left ventricle. Curve III shows systolic inhalation and curve IV shows diastolic inhalation.

In order to perform pulse-synchronized ventilation, the contraction time (systole) of the heart must be determined. The beginning of systole can be derived from the QRS complex of the electrocardiogram. There is no defined technical signal for the end of systole. Therefore, the following estimate is performed: a heart period consists of three pleases: contraction, relaxation, and the resting period, with each of these phases occupying approximately one-third of the total period between two heart beats with normal heart activity. The time for systole is therefore assumed to be one-third of the time between two heartbeats, i.e. between two successive QRS complexes. In order to obtain a defined synchronization, the ratio between inhalation and exhalation can be vaned. During systolic ventilation, the beginning of inhalation is determined from the QRS complex of the EKG signal. The duration of systole is determined from the pulse frequency, which in turn is determined by the interval of the respective previous QRS complex, and from the adjusted inhalation/exhalation ratio. At the end of systole, a switch is made to exhalation and a new QRS signal is awaited to start a new inhalation.

In diastolic inhalation, exhalation is started with a QRS complex in the EKG signal. The moment of beginning of inhalation is determined from the pulse frequency, which is determined from two previous ORS complexes, as well as from the I/E ratio. When this point is reached, a switch is made to inhalation. Then the next QRS complex is awaited again. In systolic ventilation, therefore, the beginning of the inhalation phase is synchronous with the QRS complex, while in diastolic ventilation the end of inhalation is synchronous with the QRS complex.

During inhalation, the expiration valve is closed and the fresh gas flows into the lungs. During exhalation, the expiration valve is open and the alveolar gas is entrained and carried away from the lungs by the flow of fresh gas.

Figure 24:
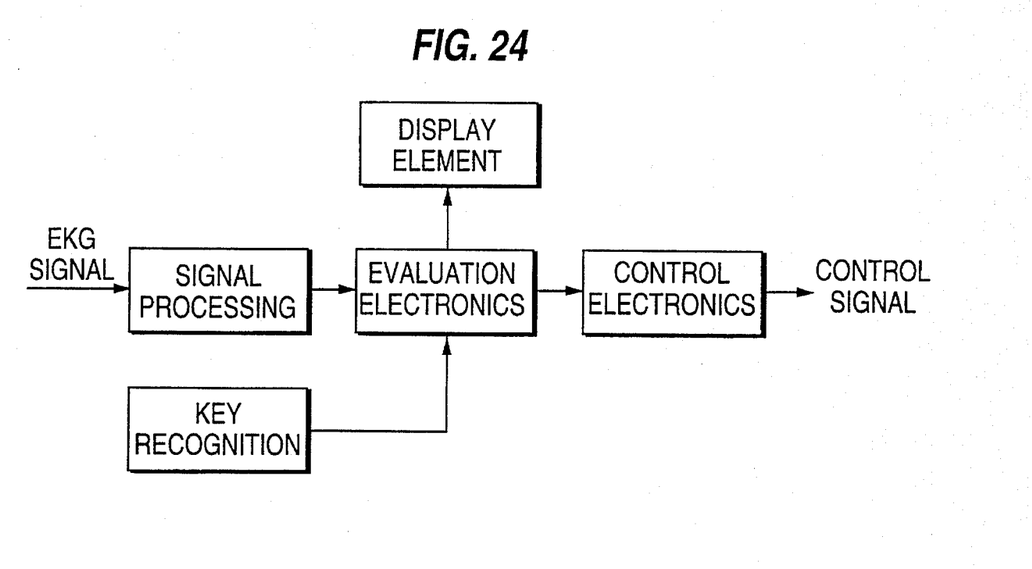
FIG. 24 is the design and functional diagram of the control device for control according to FIG. 23.

The functional design of the control device for performing pulse-synchronized ventilation according to FIG. 23 is shown in FIG. 24. The control device contains signal preparation, evaluating electronics, control electronics, and display elements and operating elements (key recognition). The signal-preparation electronics has the task of receiving the electrical EKG signal delivered by the electrocardiograph or blood pressure measuring device, encoding it, and displaying the QRS complex in order then to deliver a defined control pulse to the evaluation electronics. The signal preparation electronics contains a threshold value detector and a timer which provides a control pulse with the necessary length and amplitude. This makes it possible to use EKG devices with analog or digital signals. In this way it is possible to use all commercial EKG units or blood pressure measuring devices for the ventilator system according to the invention for pulse-synchronized ventilation.

The evaluation electronics is the central component of the control device. The evaluation electronics contains the following functional units: central processing unit, clock, RAM, interfaces for inputs and outputs, timer, interruption-control circuit, and possibly a read-only memory (ROM). The evaluation electronics receives the pulse delivered by the signal preparation electronics and, from the duration of the AZ interval of two ORS complexes, calculates the duration between two heartbeats. The evaluation electronics is also connected with the operating elements, with which the inhalation/exhalation ratio as well as the operating mode may be determined, and it monitors the display elements. In the evaluation electronics, the duration of inhalation and exhalation corresponding to the set inhalation/exhalation ratio is determined, as well as the time between the EKG signals and the operating mode to be used. The evaluation electronics transmits the required signal for opening and closing the expiration valve. Control for the expiration valve is provided as a function of the pulse frequency (EKG signals) and the set predetermined inhalation/exhalation ratio (FE ratio). With the FE ratio, the ventilation cycle can be synchronized with the systole or diastole. In contrast to a EKG trigger with initially adjustable, then fixed delay, with the control device and its control according to the invention, independence from the heart rate is ensured. It is possible to perform ventilation with a freely selectable frequency. The ratio between the inhalation and exhalation time is adjustable, for example in a range from 1:4 to 4:1. The duration of inhalation and exhalation is determined by the set FE ratio. The correct point in time for switching from inhalation to exhalation, i.e. the opening of the expiration valve, results from the set mode (systolic or diastolic inhalation) and the set I/E ratio. The control electronics performs the necessary adjustments to the control signal supplied by the evaluation electronics, in order to control the expiration valves of commercially available ventilators. The key recognition of the control device makes it possible to use operating elements to set the ratio of inhalation to exhalation. In addition, operating elements are provided for adjusting the operating mode. Key recognition is detected in the evaluation electronics and changed.

The control device also has display elements for displaying the operating mode, the set I/E ratio. In addition, incoming QRS complexes (EKG signals) as well as the position of the expiration valve are displayed. All the display elements are controlled by the central evaluation electronics of the control device. The evaluation electronics of the control device require an external program.

The control device distinguishes between two operating modes.

"Systolic" operating mode: inhalation takes place during systole.

"Diastolic" operating mode: inhalation takes place during diastole.

It is possible to switch between the two operating modes by means of operating elements; for this purpose the evaluation electronics can be controlled by key recognition; see FIG. 24.

In the "diastolic" operating mode, immediately after an EKG signal is recognized (QRS complex), the expiration valve is opened; see FIG. 23, curve IV.

Depending on the FE ratio, the expiration valve is then closed again after a certain period of time ta, so that inhalation takes place during diastole. After the next QRS complex arrives, the expiration valve is opened again.

In the "systolic" operating mode, following recognition of the QRS complex, the expiration valve is closed; see FIG. 23, curve III. In this operating mode, depending on the FE ratio, the expiration valve is opened again after a certain period of time tb, so that inhalation takes place during systole. After the next QRS complex arrives, the expiration valve is closed again.

The control device monitors the actual functionality itself. In order to achieve maximum safety, the monitoring functions of the connected ventilator system are active. If improper functioning of the ventilator system is detected, the control device is switched off automatically and the conventional ventilator begins independently to provide conventional ventilation.

The evaluation electronics of the control device constantly tests the times for inhalation and exhalation and the arrival of new EKG signals. Only when several correct ventilation cycles have been recorded does the control unit take over the monitoring of the ventilator. Then the shutoff to the ventilator is closed, indicated by a pilot light. In the event of power failure, the shutoff disconnects the control device from the ventilator, which then starts operating independently again.

In the event of an absence of EKG signals, continuation of conventional ventilation with the ventilator is likewise initialed without control by the control device, until new EKG pulses reach the control device.

To avoid dangerous pressures in the lungs, the inhalation time is monitored. In cases of excessive inhalation times, the ventilator likewise automatically takes over control once again, i.e. the control device is switched off. In those cases in which the EKG pulses arrive too rapidly, efficient ventilation is no longer guaranteed. In this case as well, the control device can shut off automatically and the conventional ventilator automatically takes over further ventilation. In the event of EKG pulses following one another at intervals that are too short, however, several such short pulses must follow one another to trigger a shutoff, since only then do they indicate a prolonged state.

To monitor the central airway pressure, the tube is provided near the distal end, on the outside, with a pressure sensor, especially an electronic pressure sensor, equipped with an electronic device for signal processing of the measured values detected. In addition, the electronic pressure sensor can supply the recorded measured value of the central airway pressure in the trachea to the control device. Then the control device, in addition to the given safety mechanisms, can monitor the function of the overall system and correct it as necessary. Further details of the provision of a tube with an external pressure sensor are described in German Patent Application P 43 10 799.0. In addition, it is possible with the aid of the central airway pressure measured continuously in the trachea using the tube with integrated pressure sensor and the electrical signals obtained therefrom, to operate the ventilator system as a function of the prevailing central airway pressure of the patient. In particular, it is possible to supply the electrical signals, corresponding to the central airway pressure determined, to the ventilator system to actuate a trigger for a defined pressure drop in the ventilator system. With continuously controlled mechanical ventilation of a patient, the electrical signals recorded, which correspond to the measured central airway pressure, can be fed into the ventilator system to control the pressure limitation and upper pressure limit functions, so that the ventilator system, when a predetermined pressure is reached, either shuts off the supply of fresh gas or switches to exhalation. In particular, capacitive pressure sensors with integrated electronic signal processing are suitable, manufactured as ready-to-install modules. The pressure sensors operate using the difference principle, i.e. pressure differences are determined and converted into electronic signals. The analog signals from the measured parameters are converted into digital signals with the aid of an analog-digital converter, amplified, and evaluated in microprocessors. These electronics are designed in the form of a chip and connected with the pressure sensor as a measurement sensor to form a small module, measuring 9×1.2×0.8 mm for example, so that they can be mounted or installed easily on the outside of the tube wall.

The control device can also be designed according to the invention in such fashion that it is capable of controlling the expiration valve in such manner that a definite positive-end expiratory pressure (PEEP) can be adjusted for the patient.

In order to adjust the PEEP, the expiration valve is opened only partially, so that a corresponding certain residual pressure PEEP remains in the airways.

The PEEP can be adjusted using the operating elements in the evaluation electronics of the control device; see FIG. 24. The evaluation electronics is capable of calculating the degree of opening of the expiration valve that is then required. This extension stage for the adjustment of the PEEP can be used on all ventilators that have a controllable expiration valve.

When pressure sensors are used in conjunction with the tube, it is possible to design the control device so that it can measure the exhalation pressure with the aid of the pressure sensors on the exhalation leg of the ventilator build-up, and this measurement signal is used in evaluation to increase the reliability of the overall system. In addition, it is also possible to use the pressure sensors to monitor the adjusted PEEP.

While in conventional ventilators the expiration valve has heretofore formed a single unit with the fresh gas source and the corresponding operating and adjusting elements, and the control device according the invention is connected in addition, it is also possible to equip the control device according to the invention directly with an expiration valve of its own. In this manner, the expiration valve together with the control device is independent of the ventilator system and can likewise perform ventilation itself.

Figure 25:
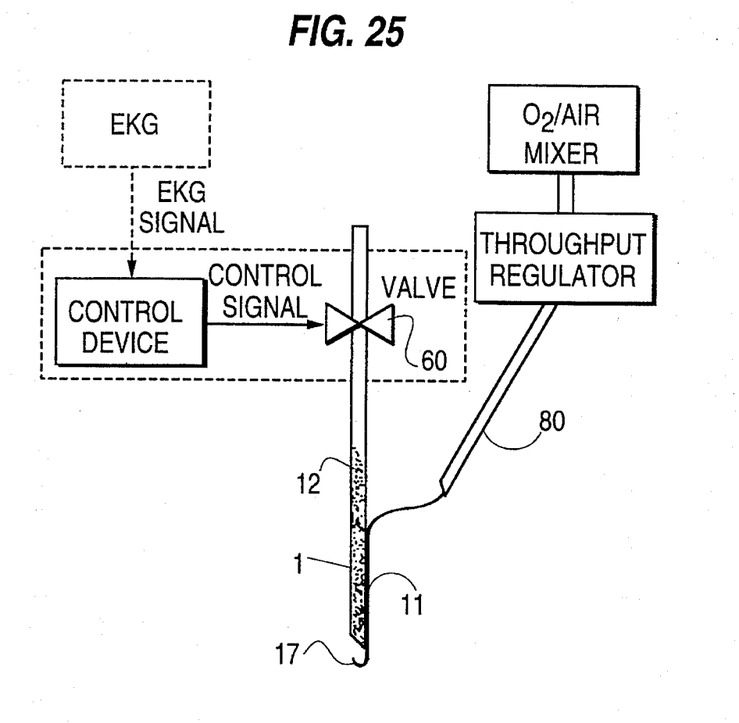
FIG. 25 is a functional diagram of a control device with integrated expiration valve for control according to FIG. 23.

FIG. 25 shows schematically the diagram of a control device with an internal expiration valve 60. The double-lumen tube 1 with ventilation passage 12 and inspiration passage as well as nozzle 17 at the transition of the distal end of the inspiration passage to the exhalation passage is used, with the aid of the control device, for pulse-synchronized ventilation with a retrograde gas flow. With an oxygen/air mixer, the correct gas mixture is selected from the oxygen/ air supply, the desired fresh gas flow can be set with the flow regulator, and fed through line 80 to inspiration passage 11. The control device which uses the EKG signals obtained from the electrocardiograph EKG unit to control ventilation, controls directly the expiration valve 60 mounted at the proximal outlet of ventilation passage 12. An arrangement according to FIG. 25 permits pulse-synchronized ventilation with continuous exhalational retrograde flow only with an expiration valve, but without a conventional ventilator. In order to be able to operate the control device completely independently, i.e. even without a EKG unit or blood pressure measuring device, according to the invention an internal clock is provided that is associated with the control device. The design of a control device with an internal clock is shown in the block diagram in FIG. 26. Instead of an electrocardiogram or blood pressure measuring device, a clock is provided. The pulses generated by the clock are picked up by the evaluation electronics. From the clock frequency and the set FE ratio, the evaluation electronics calculates the time for opening and closing the expiration valve. The operating elements and the evaluation electronics can be used to adjust the clock frequency for example between 2/min and 200/min. The control unit with the clock can be integrated for example into the system according to FIG. 25, so that the EKG device shown there can be eliminated. In this manner it is possible to provide a ventilator system that may be used as a stand-alone version, in other words without a conventional ventilator. When a clock is used in conjunction with the control device, see FIG. 26, non-pulse-synchronized ventilation with a continuous exhalational retrograde gas flow is also possible.

The control device according to the invention, in the various expansion stages, serves to control pulse-synchronized ventilation with continuous retrograde gas flow in conjunction with a double-lumen tube, in which the inspiration passage is equipped at the distal end with a nozzle that blows into the distal outlet opening of the ventilation passage. With the aid of the control device, an expiration valve that is provided either externally in a commercially available ventilator or is connected internally directly with the control device, see FIG. 25, is opened and closed. The control for the exhalation device is provided pulse-synchronously, so that inhalation takes place during either systole or diastole. In order to record the phases of the heart, the control device is connected with an EKG unit or a blood pressure measuring device.

Figure 26:
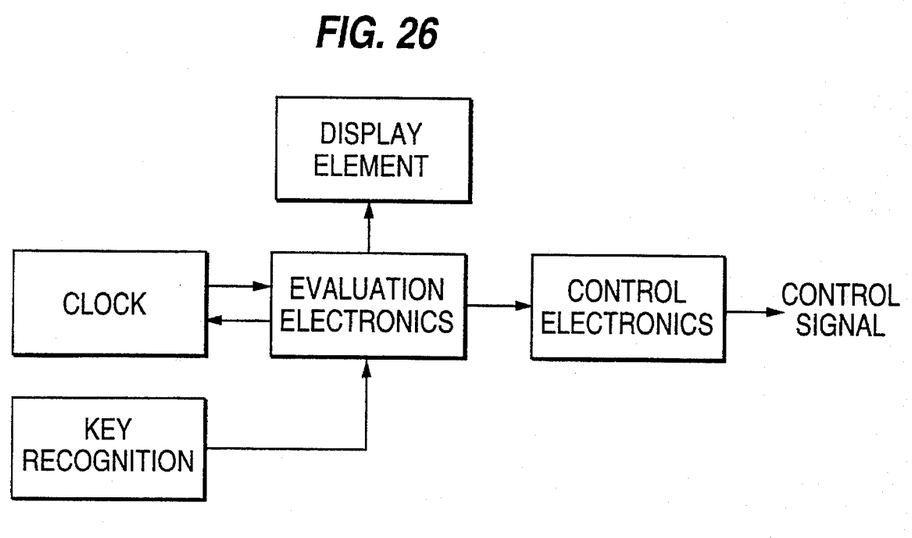
FIG. 26 is a schematic diagram of a control device for the expiration valve with an integrated clock.

The control device is designed so that it can also be operated as a stand-alone device with an integrated expiration valve and its own clock (asynchronous); see FIG. 26. In addition, the residual pressure in the airways can be adjusted with this device. Direct measurement and control of central airway pressure using pressure sensors is also possible.

I claim:

1. A tube for introduction into a respiratory tract of a patient, especially an orotracheal or nasotracheal tube or tracheostomy tube for controllable ventilation of a patient, said tube comprising a distal end that can be introduced into a respiratory tract and a proximal end provided with connections, and two passages extending essentially from the proximal end to the distal end of the tube, with one of the two passages serving as a ventilation passage during ventilation or breathing and the other of the two passages serving as a inspiration tube for additional or sole administration of fresh gas, each of the two passages having a distal outlet opening at the distal end of the tube and the distal end of the inspiration passage being bent in the vicinity of the distal end of the tube by approximately 180° and being directed toward the ventilation passage in a direction of the proximal end of the tube, thereby deflecting a flow of gas in the inspiration passage in the direction of the ventilation passage, the distal end of the inspiration passage is narrowed thereby forming a nozzle and is terminated at a nozzle distal outlet opening and said nozzle distal outlet opening is directed toward the open distal outlet end of the ventilation passage, said distal end of said inspiration passage providing means for increasing a flow of gas therethrough.

2. A tube according to claim 1, wherein one of the two passages has a smaller cross section than the other of the two passages of the tube, and the passage with the cross section that is larger relative to the passage of the other comprises the ventilation passage for ventilation and breathing and the passage with the cross section that is smaller than the other passage comprises the inspiration passage for the additional or sole fresh gas supply.

3. A tube according to claim 2, wherein the ventilation passage and the inspiration passage are divided from one another by a partition in tube.

4. A tube according to claim 1, wherein the ventilation passage has size to allow introduction of a suction catheter or bronchoscope.

5. A tube according to claim 1, wherein one of the two passages has a smaller cross section than the other of the two passages of the tube, and the passage with the cross section that is larger than that of the other passage comprises the ventilation passage for ventilation and breathing and the passage with the cross section that is smaller than that of the other passage comprises the inspiration passage for the additional or sole fresh gas supply, with sizes of cross sections of the ventilation passage, the inspiration passage, and the distal nozzle outlet opening have a ratio of approximately 8:2:1.

6. A tube according to claim 1, wherein the distal outlet opening of the ventilation passage runs diagonally to a lengthwise axis of the tube, so that the distal end of the tube is beveled unilaterally in the vicinity of the ventilation passage toward the distal end of the tube.

7. A tube according to claim 1, wherein the nozzle distal outlet opening of the inspiration passage is located off center relative to the outlet opening of the ventilation passage near the periphery of the ventilation passage.

8. A tube according to claim 1, wherein the nozzle distal outlet opening of the inspiration passage and distal outlet opening of the ventilation passage abut one another so that at the point where outlet opening of ventilation passage terminates a portion of the nozzle distal outlet opening of the inspiration passage is located.

9. A tube according to claim 1, wherein the nozzle distal outlet opening of the inspiration passage is located outside the distal outlet opening of the ventilation passage and outside the ventilation passage.

10. A tube according to claim 1, wherein the nozzle distal outlet opening of the inspiration passage partially projects into ventilation passage through distal outlet opening of ventilation passage.

11. A tube according to claim 1, wherein at the distal end of the tube, a nozzle-shaped piece is connected with the tube as an extension of inspiration passage, said piece forming a nozzle channel which comprises an end portion of the inspiration passage to provide a nozzle-shaped taper in the inspiration passage and the nozzle distal outlet opening.

12. A tube according to claim 11, wherein the nozzle-shaped piece is bent at right angles twice, so that the flow path of the inspiration passage is deflected about 180°.

13. A tube according to claim 12, wherein the nozzle distal outlet opening formed by the nozzle-shaped piece for the inspiration passage extends beveled in a plane which is at an angle to or perpendicular to a bevel of the outlet opening of the ventilation passage.

14. A tube according to any one of claims 11, 12 or 13, wherein the nozzle-shaped piece is inserted with one leg into an open end of inspiration passage at the distal end of the tube and is secured to a wall of the tube.

15. A tube according to claim 1, wherein a pressure sensor is mounted near the distal end of the tube.

16. A tube according to claim 15, wherein the pressure sensor mounted near the distal end of tube is mounted externally on or in a wall of the tube in a position for measuring pressure outside the tube.

17. A tube according to claim 15 or 16, wherein an electronic pressure sensor is provided, equipped with integrated electronic measured value detection and signal processing for continuous measurement of the central airway pressure prevailing in the trachea of the patient which can be connected through a line with a control device for a ventilator to control the ventilator as a function of the central airway pressure prevailing in the trachea of a patient.

18. A tube according to claim 1, wherein near the distal end of the ventilation passage, the cross section of the ventilation passage is reduced by 10 to 25% for a short distance relative to the lengthwise extent of exhalation passage, whereby a flow of gas is increased therethrough.

19. A ventilator system for electrically controllable mechanical ventilation of a patient with fresh gas, with a tube insertable into a respiratory tract of a patient, according to claim 1, with the ventilation passage of tube being connected at its proximal end to a controllable expiration valve and with inspiration passage being connected at its proximal end to a fresh gas source.

20. A ventilator according to claim 19, wherein the expiration valve is part of a conventional ventilator with a fresh gas source.

21. A ventilator system according to claim 19, wherein an electrical control device is provided to control expiration valve.

22. A ventilator system according to claim 21, wherein the control device is automatically switchable upon recognition of improper functioning of mechanical ventilation of the electrocardiograph.

23. A ventilator system according to claim 22, wherein the control device is connected to the pressure sensor integrated into the tube to monitor the central airway pressure.

24. A ventilator system according to claim 21, wherein a defined positive end-expiratory pressure (PEEP) for the patient can be adjusted by controlling the expiration valve for partial opening by means of the control device.

25. A ventilator system according to claim 21, wherein the control device is connected with the expiration valve to form a structural unit.

26. A ventilator system according to claim 19 or 21, wherein the electrical control device for the expiration valve is connected to an electrocardiograph or blood pressure measuring device and, depending on the output signals delivered by the electrocardiograph or blood pressure measuring device, the expiration valve is controllable so that ventilation of the patient with fresh gas supplied through the inspiration passage of tube can be performed, synchronized with the pulse, with a retrograde flow.

27. A ventilator system according to claim 26, wherein the expiration valve is controllable as a function of the pulse frequency and an adjustable inhalation/exhalation ratio.

28. A ventilator system according to claim 26, wherein the control device is equipped with electronic signal preparation of the electrical signal delivered by the electrocardiograph or blood pressure measuring device, and with electronic evaluation for the processed received signal and electronic control for the control signal to be delivered to the expiration valve, as well as operating elements for operating modes and display elements.

29. A ventilator system according to claim 28, wherein the control device for the expiration valve has operating elements for changing the time ratio from inhalation to exhalation as well as for the alternative selection of synchronization of inhalation with contraction of the heart muscle (systolic inhalation) or with relaxation of the heart muscle (diastolic inhalation).

30. A ventilator system according to claim 28, wherein the electrocardiograph or blood pressure measuring device supplying signals for the control device is replaced by a clock supplying corresponding signals with adjustable clock frequency of the signals.

31. A ventilator system according to claim 19, wherein an electrically controllable pressure reduction valve is provided in the supply line for the fresh gas to the inspiration passage of tube, with the fresh gas flow into the inspiration passage being freely selectable and controllable during inhalation and exhalation.

32. A ventilator system according to claim 31, wherein the electrically controllable pressure-reduction valve is connected to the electronic control device connected to the electrocardiograph or blood pressure measuring device, and is controllable as a function of the signals delivered by the electrocardiograph or blood pressure measuring device.

33. A ventilator system claim 31 or 32, wherein the inhalational fresh gas flow is adjustable to the minute volume required for carbon dioxide elimination by controlling the pressure-reduction valve with the aid of a control device, and the exhalational gas flow is adjustable to the mean airway pressure that is critical for oxygenation by controlling the pressure reduction valve with the aid of the control device.

34. A tube according to claim 1, wherein the cross sectional area of the inspiration passage of the tube is reduced at the distal end up to the nozzle distal outlet opening by approximately one-half.

35. A tube according to claim 1, wherein a nozzle-forming means is inserted into a portion of the distal end of the tube forming the inspiration passage, and at least a portion of the nozzle-forming means extends outside of the ventilation passage.

36. A tube according to claim 1, wherein the ventilation passage includes means for increasing a flow of gas therethrough.

* * * * *